United States Patent
Indravudh et al.

(10) Patent No.: US 8,099,171 B2
(45) Date of Patent: Jan. 17, 2012

(54) IMPLANTABLE MEDICAL LEAD CONFIGURED FOR IMPROVED MRI SAFETY AND HEATING REDUCTION PERFORMANCE

(75) Inventors: Virote Indravudh, Santa Clarita, CA (US); Yong D. Zhao, Simi Valley, CA (US); Kevin L. Morgan, Simi Valley, CA (US); Dion F. Davis, Acton, CA (US); Grace Jang, Calabasas, CA (US)

(73) Assignee: Pacesetter, Inc., Sylmar, CA (US)

( * ) Notice: Subject to any disclaimer, the term of this patent is extended or adjusted under 35 U.S.C. 154(b) by 392 days.

(21) Appl. No.: 12/495,612

(22) Filed: Jun. 30, 2009

(65) Prior Publication Data

US 2010/0331940 A1 Dec. 30, 2010

(51) Int. Cl.
*A61N 1/00* (2006.01)
(52) U.S. Cl. .......................................... 607/116
(58) Field of Classification Search .................. 607/116, 607/37, 63, 115; 33/175
See application file for complete search history.

(56) References Cited

U.S. PATENT DOCUMENTS

| | | | |
|---|---|---|---|
| 6,871,091 B2 | 3/2005 | Wilkinson et al. | |
| 6,944,489 B2 | 9/2005 | Zeijlemaker et al. | |
| 7,751,903 B2 * | 7/2010 | Stevenson et al. | 607/63 |
| 2003/0083723 A1 | 5/2003 | Wilkinson et al. | |
| 2003/0083726 A1 | 5/2003 | Zeijlemaker et al. | |
| 2005/0222659 A1 | 10/2005 | Olsen et al. | |
| 2007/0208383 A1 | 9/2007 | Williams | |
| 2007/0299490 A1 | 12/2007 | Yang et al. | |
| 2008/0049376 A1 | 2/2008 | Stevenson et al. | |
| 2008/0116997 A1 * | 5/2008 | Dabney et al. | 333/182 |

FOREIGN PATENT DOCUMENTS

| | | |
|---|---|---|
| WO | 03037424 A2 | 5/2003 |
| WO | 03037424 A3 | 5/2003 |
| WO | 03063946 A2 | 8/2003 |
| WO | 03063946 A3 | 8/2003 |
| WO | 2006093685 A1 | 9/2006 |
| WO | 2007047966 A2 | 4/2007 |
| WO | 2007047966 A3 | 4/2007 |
| WO | 2007145671 A2 | 12/2007 |
| WO | 2007145671 A3 | 12/2007 |

\* cited by examiner

*Primary Examiner* — George Manuel
*Assistant Examiner* — Robert Wieland (57) ABSTRACT

An implantable medical lead configured for improved MRI safety and heating reduction performance is disclosed herein. In one embodiment, the lead includes a tubular body having a proximal end and a distal end with a lead connector near the proximal end. In this embodiment the lead further includes a conductor extending longitudinally within the tubular body and having a proximal end that is electrically coupled to the connector and a distal end electrically coupled to a contact pin. The lead in this embodiment further includes a filter element electrically coupled to a distal end of the contact pin and a flange electrically coupled between a proximal end of the filter element and a proximal portion of an electrode. In this embodiment the flange and the proximal portion of the electrode form at least a first part of a hermetic chamber enclosing the filter element.

15 Claims, 10 Drawing Sheets

IMPLANTABLE MEDICAL LEAD CONFIGURED FOR IMPROVED MRI SAFETY AND HEATING REDUCTION PERFORMANCE

FIELD OF THE DISCLOSURE

The present invention relates to medical apparatus and methods. More specifically, the present invention relates to implantable cardiac electrotherapy leads and methods of manufacturing and using such leads.

BACKGROUND

Current implantable medical leads for use with implantable pulse generators, such as pacemakers, defibrillators, implantable cardioverter defibrillators ("ICD") or neurostimulators, are prone to heating and induced current when placed in the strong magnetic (static, gradient and RF) fields of a magnetic resonance imaging ("MRI") machine. The heating and induced current are the result of the lead acting like an antenna in the magnetic fields generated during an MRI. Heating and induced current in the lead may result in deterioration of stimulation thresholds or, in the context of a cardiac lead, even increase the risk of cardiac tissue perforation and damage.

Over fifty percent of patients with an implantable pulse generator and implanted lead require, or can benefit from, an MRI in the diagnosis or treatment of the medical condition. MRI modality allows for flow visualization, characterization of vulnerable plaque, non-invasive angiography, assessment of ischemia and tissue perfusion, and a host of other applications. The diagnosis and treatment options enhanced by MRI are only going to grow over time. For example, MRI has been proposed as a visualization mechanism for lead implantation procedures.

There is a need in the art for an implantable medical lead configured to improve MRI safety and heating reduction performance. There is also a need in the art for methods of manufacturing and using such a lead.

BRIEF SUMMARY

An implantable medical lead configured for improved MRI safety and heating reduction performance is disclosed herein. In one embodiment, the lead includes a tubular body having a proximal end and a distal end with a lead connector near the proximal end. In this embodiment the lead further includes a conductor extending longitudinally within the tubular body and having a proximal end that is electrically coupled to the connector and a distal end electrically coupled to a contact pin. The lead in this embodiment further includes a filter element electrically coupled to a distal end of the contact pin and a flange electrically coupled between a proximal end of the filter element and a proximal portion of an electrode. In this embodiment the flange and the proximal portion of the electrode form at least a first part of a hermetic chamber enclosing the filter element.

In another embodiment, the lead includes a tubular body having a proximal end and a distal end with a lead connector near the proximal end. In this embodiment the lead further includes a conductor extending longitudinally within the tubular body and having a proximal end that is electrically coupled to the connector and a distal end electrically coupled to a conductive coupler. In this embodiment a proximal end of a filter element is electrically coupled to a distal end of the conductive coupler and an electrode is electrically coupled to a distal end of the filter element. In this embodiment the lead further includes a non-electrically conductive shell enclosing at least a portion of the filter element and longitudinally spacing the conductive coupler from the electrode, wherein the non-electrically conductive shell forms at least part of a hermetic chamber enclosing the filter element.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Disclosed herein is an implantable medical lead 10 configured for improved MRI safety and heating reduction performance. In various embodiments, the lead 10 includes a tubular body 50 with proximal and distal ends 40, 45, and a filter assembly 95 near, at or within the lead distal tip 70. In some embodiments, the filter assembly 95 may include a lumped inductor or discrete inductor-capacitor filter 230. In some embodiments, the filter assembly 95 may be at the proximal end of the lead. The filter 230 of the filter assembly 95 may reduce the temperature increase caused by an induced current thereby reducing the effects caused by the heating of the lead 10, which may result in deterioration of stimulation thresholds or, in the context of a cardiac lead, a possible increase in the risk of cardiac tissue perforation and damage.

In some embodiments, the filter 230 functions to control the temperature increase such that the temperature increase is less than 2° C. In various embodiments, the filter assembly 95 is compact in size but still maintains functionality. That is, the filter 230 will generally operate at or close to its self resonant frequency and exhibit sufficient impedance under the MRI scan frequencies of 64 MHz (1.5 T) and 128 MHz (3.0 T). The filter assembly 95 is compatible with both passive and active fixation leads, has a low to minimal impact on lead pacing or defibrillation functions, and may be effectively manufactured and assembled with existing technology with increased efficiency and at a reduced cost.

Figure 1:
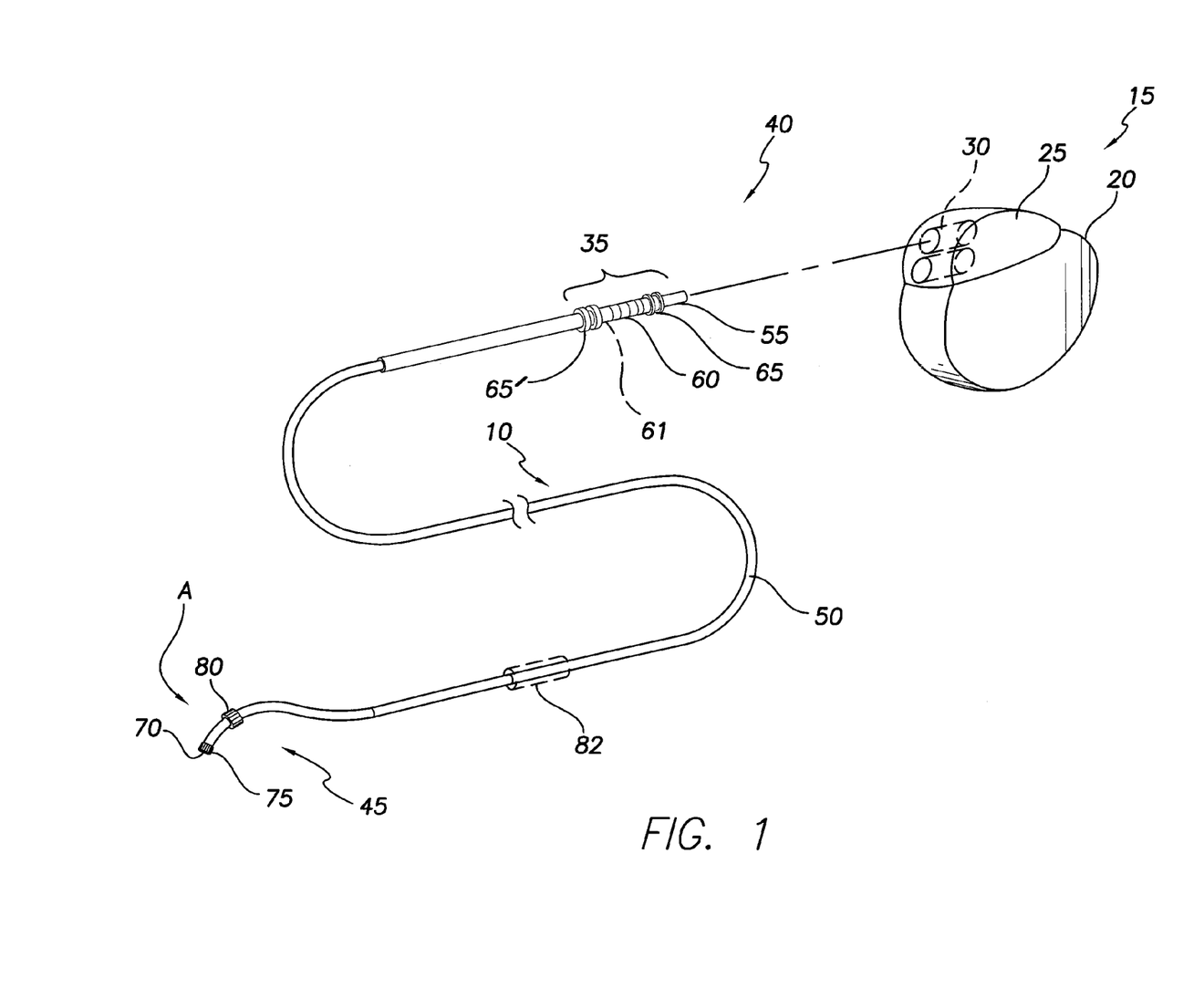
FIG. 1 is an isometric view of an implantable medical lead and a pulse generator for connection thereto.

For a general discussion of an embodiment of a lead 10 configured for improved MRI safety and heating reduction performance, reference is made to FIG. 1, which is an isometric view of an implantable medical lead 10 and a pulse generator 15 for connection thereto. The pulse generator 15 may be a pacemaker, defibrillator, implantable cardioverter defibrillator ("ICD") or neurostimulator. As indicated in FIG. 1, the pulse generator 15 may include a can 20, which may house the electrical components of the pulse generator 15, and a header 25. The header may be mounted on the can 20 and may be configured to receive a lead connector end 35 in a lead receiving receptacle 30.

As shown in FIG. 1, in one embodiment, the lead 10 may include a proximal end 40, a distal end 45 and a tubular body 50 extending between the proximal and distal ends. In some embodiments, the lead may be a 6 French, model 1688T lead, as manufactured by St. Jude Medical of St. Paul, Minn. In other embodiments, the lead may be a 6 French model 1346T lead, as manufactured by St. Jude Medical of St. Paul, Minn. In other embodiments, the lead 10 may be of other sizes and models.

As indicated in FIG. 1, the proximal end 40 may include a lead connector end 35 including a pin contact 55, a first ring contact 60, a second ring contact 61, which is optional, and sets of spaced-apart radially projecting seals 65. In some embodiments, the lead connector end 35 may include the same or different seals and may include a greater or lesser number of contacts. The lead connector end 35 may be received in a lead receiving receptacle 30 of the pulse generator 15 such that the seals 65 prevent the ingress of bodily fluids into the respective receptacle 30 and the contacts 55, 60, 61 electrically contact corresponding electrical terminals within the respective receptacle 30.

As illustrated in FIG. 1, in one embodiment, the lead distal end 45 may include a distal tip 70, a tip electrode 75 and a ring electrode 80. As shown and discussed in more detail below with regard to FIGS. 8A-8B, in some embodiments, the lead distal end 45 may include a helical anchor 605 that is extendable from within the distal tip 70 and may or may not act as an electrode.

As shown in FIG. 1, in some embodiments, the distal end 45 may include a defibrillation coil 82 about the outer circumference of the lead body 50. The defibrillation coil 82 may be located proximal of the ring electrode 80.

The tip electrode 75 may form the distal tip 70 of the lead body 50. The ring electrode 80 may extend about the outer circumference of the lead body 50, proximal of the distal tip 70. In other embodiments, the distal end 45 may include a greater or lesser number of electrodes 75, 80 in different or similar configurations.

Figure 2A:
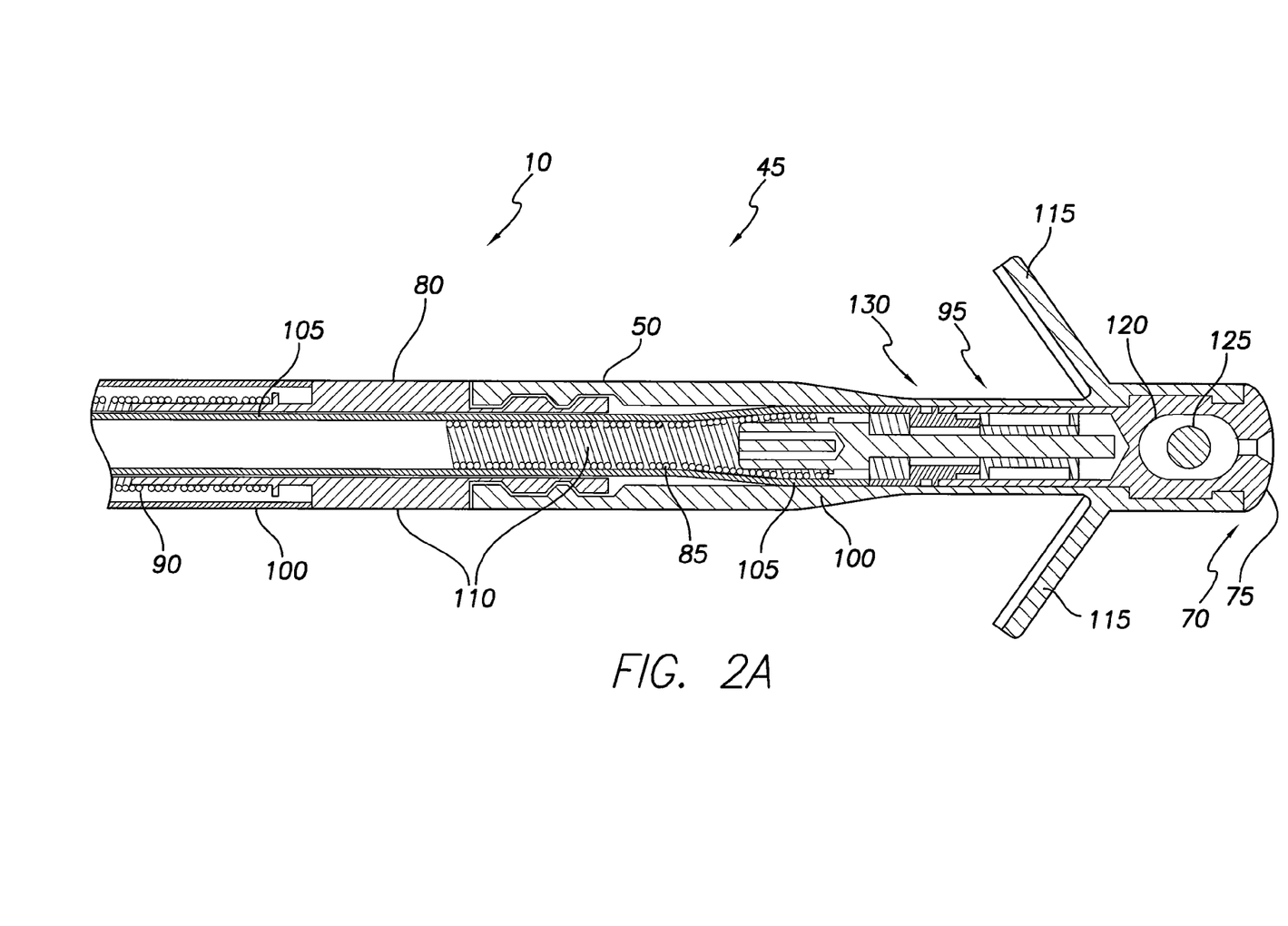
FIG. 2A is a longitudinal cross-sectional view of a distal segment of a lead tubular body of one embodiment of the lead having a filter assembly inside the lead in the vicinity of arrow A in FIG. 1.

In one embodiment, the tip electrode 75 may be in electrical communication with the pin contact 55 via electrical conductors 85 (see FIG. 2) and the ring electrode 80 may be in electrical communication with the first ring contact 60 via other electrical conductors 90 (see FIG. 2). In some embodiments, the defibrillation coil 82 may be in electrical communication with the second ring contact 61 via still other electrical conductors.

As discussed in more detail below, the lead inner conductor coil 85 may be connected to the tip electrode 75 via a filter assembly 95 at the distal end such that the inner conductor circuit travels through the filter 230 before it connects to the tip electrode 75, thereby filtering out the high frequency RF induced current that may result when the lead 10 is within the magnetic field of an MRI scan.

Without the novel filter assembly configurations as disclosed herein, the conductors may act as antenna in the MRI's magnetic field, which may induce a current. An induced current may cause the conductors or the electrodes connected thereto to heat or stimulate, which may cause damage to the lead or the tissue that is in contact with the electrodes.

For a discussion of a first embodiment of a lead 10 having a filter assembly 95 that is configured for improved MRI safety and heating reduction performance, reference is made to FIG. 2A, which is a longitudinal cross-sectional view of a distal segment of a lead tubular body 50 of one embodiment of the lead 10 having a filter assembly 95 inside the lead 10 in the vicinity of arrow A in FIG. 1. As shown in FIG. 2A, the lead distal end 45 includes the lead body 50, a tip electrode 75, and a ring electrode 80. The body 50 may include concentrically arranged outer and inner insulation layers 100, 105 and concentrically arranged inner and outer helical conductor coils 85, 90. The inner conductor coil 85 defines a central lumen 110 that extends the length of the lead 10.

The inner insulation layer 105 isolates the inner and outer conductors 85, 90, and the outer insulation layer or jacket 100, along with the ring electrode 80, forms the outer circumferential surface of the lead body 50. Specifically, in some embodiments, the jacket 100 may extend about the outer circumference of the lead body 50, both proximal and distal of the ring electrode 80. The jacket 100 may also extend about a portion of the distal tip 70 and tip electrode 75.

As indicated in FIG. 2A, the distal tip 70 may include tines 115 proximal the tip electrode 75 that serve as a passive fixation mechanism for the lead 10 to engage nearby tissue. The tines 115 may be extensions of the material of the jacket 100. The tines 115 may be made of silicone rubber, silicone rubber-polyurethane-copolymer ("SPC"), or polyurethane.

As illustrated in FIG. 2A, in some embodiments, the tip electrode 75 may have an opening 120 defined therein wherein a steroid-eluting plug 125 is located. The steroid-eluting plug 125 may be used to reduce stimulation thresholds in a patient.

As indicated in FIG. 2A, a feedthru 130 and a filter assembly 95 may be located between the distal end of the inner conductor coil 85 and the distal tip electrode 75. The feedthru 130 and the filter assembly 95 may form an electrical pathway between the inner conductor coil 85 and the tip electrode 75 to place the conductor 85 and electrode 75 in electrical communication.

Figure 2B:
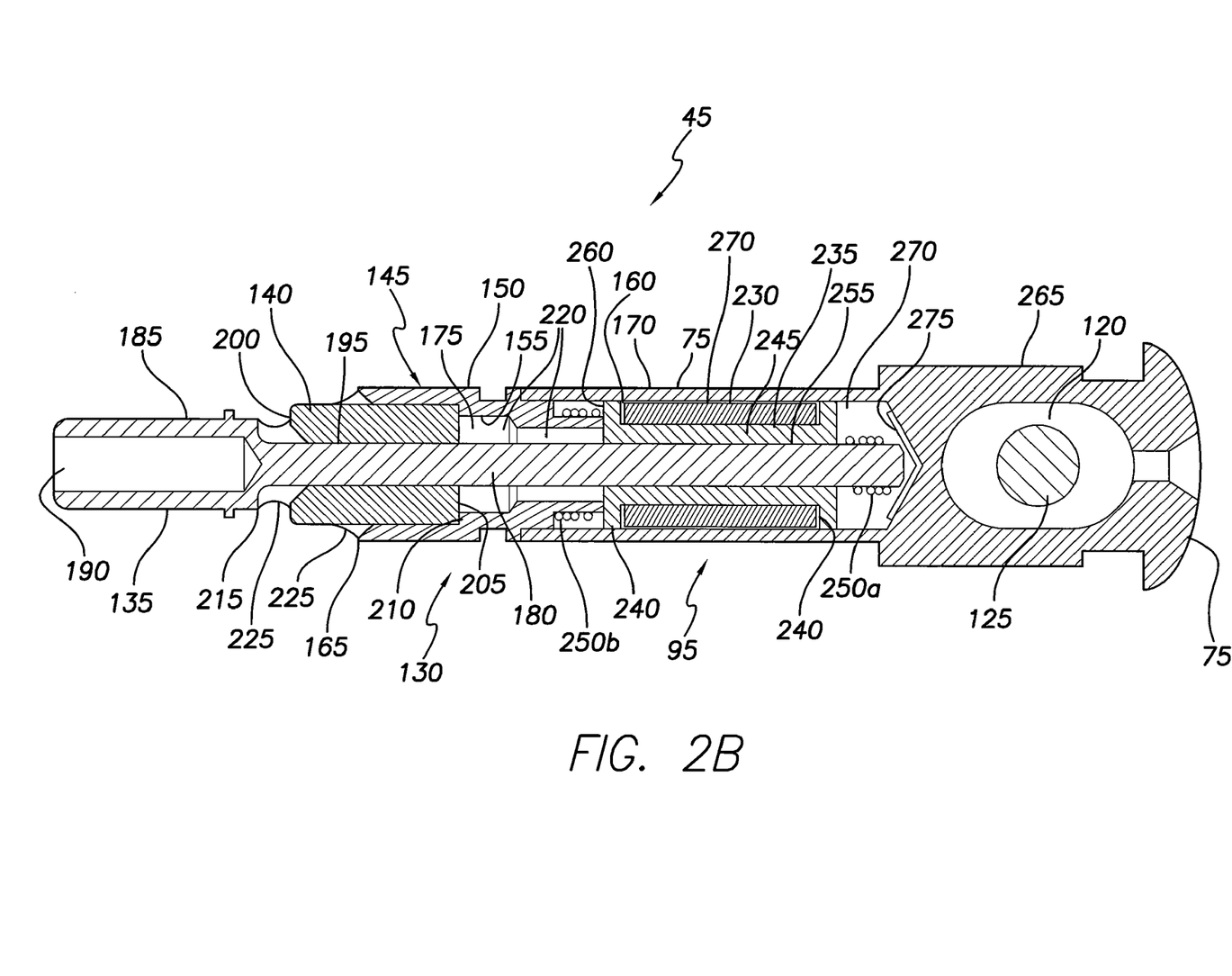
FIG. 2B is an enlarged cross-sectional view of the feedthru, filter assembly and tip electrode of FIG. 2A.
Figure 2C:
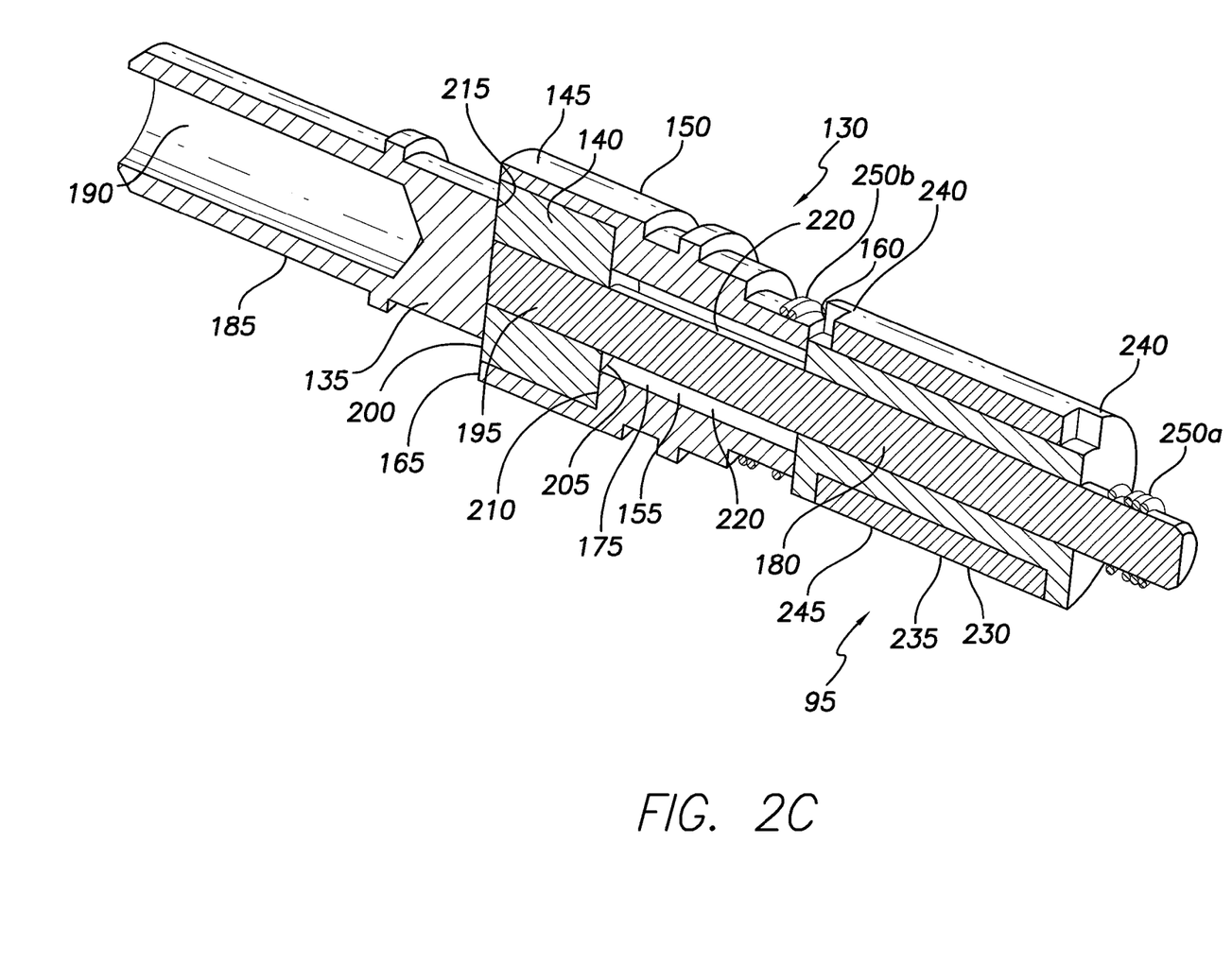
FIG. 2C is an enlarged cross-sectional isometric view of the feedthru and filter assembly of FIG. 2B, less the tip electrode.

For a more detailed discussion of the feedthru 130 and filter assembly 95, reference is made to FIGS. 2B and 2C. FIG. 2B is an enlarged cross-sectional view of the feedthru 130, filter assembly 95 and tip electrode 75 of FIG. 2A. FIG. 2C is an enlarged cross-sectional isometric view of the feedthru 130 and filter assembly 95 of FIG. 2B, less the tip electrode 75.

As indicated in FIGS. 2B and 2C, the feedthru 130 may include a contact pin 135, an insulator 140 and a flange 145. In one embodiment, the flange 145 may include an outer circumferential surface 150, an inner circumferential surface 155, a distal end 160 and a proximal end 165. The outer circumferential surface 150 may have a stepped cylindrical construction that, as indicated in FIGS. 2A-2B, may be configured on its proximal two thirds to be received in the tubular body 50 and on its distal one third to be received in a proximal cylindrical portion 170 of the tip electrode 75. The flange inner circumferential surface 155 defines an axially extending bore 175 through the flange 145 that may receive the insulator 140 and the pin 135. The flange inner circumferential surface 155 may have a stepped cylindrical construction. The flange 145 may be constructed of platinum, MP35 stainless steel, or titanium.

As shown in FIGS. 2A-2C, the contact pin 135 may include a distal cylindrical shaft portion 180 and a proximal cylindrical base portion 185. The base portion 185 may include a cylindrical void 190 extending axially in the distal direction from a most proximal end of the base portion 185. The void 190 may axially align and be a continuation of the lumen 110 such that the void 190 may receive the distal end of a guidewire or stylet extended through the lumen 110 of the lead 10. The pin 135 may be constructed of platinum, MP35 stainless steel, or titanium.

As illustrated in FIGS. 2B and 2C, the insulator 140 is a generally cylindrical body having a central bore 195, a proximal end 200, a distal end 205, and outer and inner circumferential surfaces. As shown in FIG. 2C, the insulator 140 is configured to be received in the proximal end of the flange 145 such that the outer circumferential surface of the insulator contacts the inner circumferential surface of the flange 145 in an opposed fashion and the distal end 205 of the insulator 140 contacts a proximal step 210 of the inner circumference of the flange 145 in an opposed fashion. The insulator central bore 195 extends axially through the insulator 140 and is configured to receive the cylindrical shaft portion 180 of the pin 135 such that the opposed circumferential surfaces of the shaft portion 180 and insulator central bore 195 contact in an opposed fashion and the insulator proximal end 200 and the distal end 215 of the pin base portion 185 contact in an opposed fashion. The insulator 140 may be made of any non-metallic material, including ceramics of Alumina, Sapphire, Ruby, Kryoflex or etc.

As can be understood from FIGS. 2A-2C, when the feedthru 130 is in an assembled state, in one embodiment, the insulator 140 is concentrically received in the proximal third portion of the bore 175 of the flange 145. Also, the distal end 215 of the pin base portion 185 abuts against and is joined to the proximal end 200 of the insulator 140 as the pin shaft portion 180 axially extends through the bores 195, 175 of the insulator 105 and the flange 145 in a concentric arrangement. In one embodiment, the pin shaft portion 180 extends substantially distal the distal end 160 of the flange 145. Also, the outer circumferential surface of the pin shaft portion 180 may contact the inner circumferential surface of the insulator 140, but may not contact the inner circumferential surface 155 of the flange 145, thereby creating a gap or void 220 between the opposed circumferential surfaces of the flange 145 and the pin shaft portion 180. Thus, the insulator 140 and gap 220 serve to isolate the pin 135 from direct electrical contact with the flange 145; electrical communication between the flange 145 and the pin 135 being made possible by the filter assembly 95, which is electrically located between the pin 135 and flange 145.

As can be understood from FIG. 2B, in one embodiment, the insulator 140 is joined to the flange 145 via gold brazing 225 or reflow techniques. Similarly, in one embodiment, the insulator 140 is joined to the pin 135 via gold brazing 225 or reflow techniques. Such joining of the pin 135, insulator 140 and flange 145 may form part of a hermetic seal for the combined assembly of the feedthru 130 and filter assembly 95. Joining methods such as welding, crimping, gold brazing, etc. may be used to create a hermetic seal between the flange 145 and the proximal portion 170 of the tip electrode 75, creating a hermetically sealed chamber 270 out of the bore 270 of the proximal portion 170 of the tip electrode 75. The hermetically sealed chamber 270 may prevent the exposure of the filter assembly 95 to body fluids, avoiding electrical shorting and preventing contact between body fluids and non-biostable or non-bio-compatible elements.

As can be understood from FIGS. 2A-2C, in one embodiment, the filter assembly 95 may include a filter element 230 and a non-conductive bobbin or housing 235. The filter element 230 may be an induction coil or inductor/capacitor element. Specifically, in one embodiment, the filter element 230 may be a lumped inductor of multiple-layered insulated fine wire coiled in a tightly wound fashion over the housing 235. The fine wire forming the filter element 230 may be wound about the housing 235 either parallel with or perpendicular to a center line of the pin 135. The fine wire of the filter element 230 may be single or multiple-layer insulated with conductive cores of copper, Pt/Ir, MP35N, or etc. In other embodiments, the filter element 230 may be any other type of RF filter including, for example, discrete inductor-capacitor filters, etc. Furthermore, the filter assembly 95 may include one or more filter elements 230, which may be wired in series and/or parallel.

As shown in FIGS. 2B and 2C, the housing or bobbin 235 may have flanged ends 240 and a cylindrical center 245 extending between the flanged ends 240, defining a location for receiving the wire that forms the filter element 230. The filter element wire is wound about the cylindrical center and between the flanged ends 240 of the bobbin 235. As illustrated in FIGS. 2B and 2C, the wires forming the filter element 230 may extend distally and proximally out of the housing 235 to form distal and proximal terminals 250a, 250b. In one embodiment, the terminals 250a, 250b may be in the form of coils and/or may be in the form of tined wires 250a, 250b.

As indicated in FIGS. 2A-2C, in one embodiment, the bobbin 235 includes a bore 255 extending axially through the bobbin 235. The bobbin 235 may be formed of a non-conductive material, such as ceramic, sapphire, various polymers, such as, PEEK or Delrin, or other appropriate material.

As illustrated in FIGS. 2A-2C, when the feedthru 130 and the filter assembly 95 are assembled together, the proximal end 260 of the filter assembly 94 abuts against the distal end 160 of the flange 145 and the cylindrical shaft portion 180 of the pin 135 extends through the bore 255 of the filter assembly 95 such that the shaft portion 180 distally projects out of the bore 255. The proximal tined wires 250b coil about, and are electrically coupled to, the outer circumferential surface 150 of the distal portion of the flange 145. Similarly, the distal tined wires 250a coil about, and are electrically coupled to, the outer circumferential surface of the distal end of the shaft portion 180 that distally protrudes from the bore 255 of the filter assembly 95. The bobbin 235 electrically insulates the flange 145 and the shaft portion 180 from the entirety of the wires of the filter element 230, except those specific tined wire terminals 250a, 250b extending outside the bobbin 235 to electrically couple to the pin shaft 180 and flange 145. The electrical connection between the wire terminals 250a, 250b and the respective portions of the pin 135 and the flange 145 may be formed via soldering, laser welding, conductive epoxy or other appropriate means.

As shown in FIGS. 2A-2B, in one embodiment, the electrode tip 75 may include a proximal portion 170 and a distal portion 265. The proximal portion 170 may by cylindrical and define a cylindrical bore 270 in which the filter assembly 95 and portions of the feedthru 130 are received when these components are in an assembled state. The distal portion 265 may include the aforementioned opening 120 for holding the steroid-eluting plug 125.

As indicated in FIGS. 2A-2B, when the feedthru 130, filter assembly 95 and the electrode tip 75 are assembled together, the cylindrical bore 270 of the electrode tip 75 receives therein the entirety of the filter assembly 95, the distal third of the flange 145, and a substantial portion of the shaft 180. The distal end of the shaft 180 abuts against an electrically insulative proximal-facing surface 275 of the bore 270 such that the shaft 180 and the tip electrode 75 are not in direct electrical contact, the shaft 180 and the tip electrode 75 instead having to rely on the filter element 230 to establish electrical communication between the shaft 180 and tip electrode 75. In one embodiment, the electrically insulative surface 275 may be a Kapton Tape of Polyimate® or Humiseal®. Alternatively, the electrically insulative surface 275 may be a non-conductive epoxy, dielectric coating, an electrically insulative thin film, or other appropriate insulation material.

As can be understood from FIGS. 2A-2B, the electrical circuit from the inner conductor coil 85 to the tip electrode 75 first extends along the length of the pin 135 to the pin's distal end, which is in electrical contact with the distal wire terminal 250a. The electrical circuit then extends from the distal wire terminal 250a to the proximal wire terminal 250b via the filter element 230 of the filter assembly 95. The electrical circuit then extends from the proximal wire terminal 250b to the tip electrode 75 via the flange 145, which is in electrical contact with both the proximal wire terminal 250b and the tip electrode 75. Thus, since the proximal end of the inner conductor coil 85 is in electrical communication with the pulse generator 15, the pulse generator and tip electrode are in electrical communication via the filter element 230. As the filter element 230 forms part of the electrical circuit extending between the pulse generator 15 and the tip electrode 75, the filter element 230 may reduce any current induced by the lead 10 being present in the magnetic field of a MRI scan. The filter assembly 95 may help to improve the heating reduction performance of the lead 10, thereby reducing the chance of tissue damage or perforation that may be caused by increased temperature of the lead tip electrode 75.

While the embodiment depicted in FIGS. 2A-2C may have a filter assembly 95 and feedthru 130 configured such that the filter assembly 95 makes electrical contact with the pin shaft 180 on the distal end of the filter assembly 95 and the flange 145 on the proximal end of the filter assembly 95, in other embodiments the electrical contact with the flange 145 and pin shaft 180 may be both on the proximal end of the filter assembly 95. For example, as indicated in FIG. 3, which is the same view as FIG. 2A, except of another embodiment, the feedthru 130 has the same components 135, 140, 145 and same general configuration as the embodiment depicted in FIGS. 2A-2B, except the pin shaft 180 does not extend through the filter assembly 95 or to the proximal-facing surface of the electrode tip bore 270.

Figure 3:
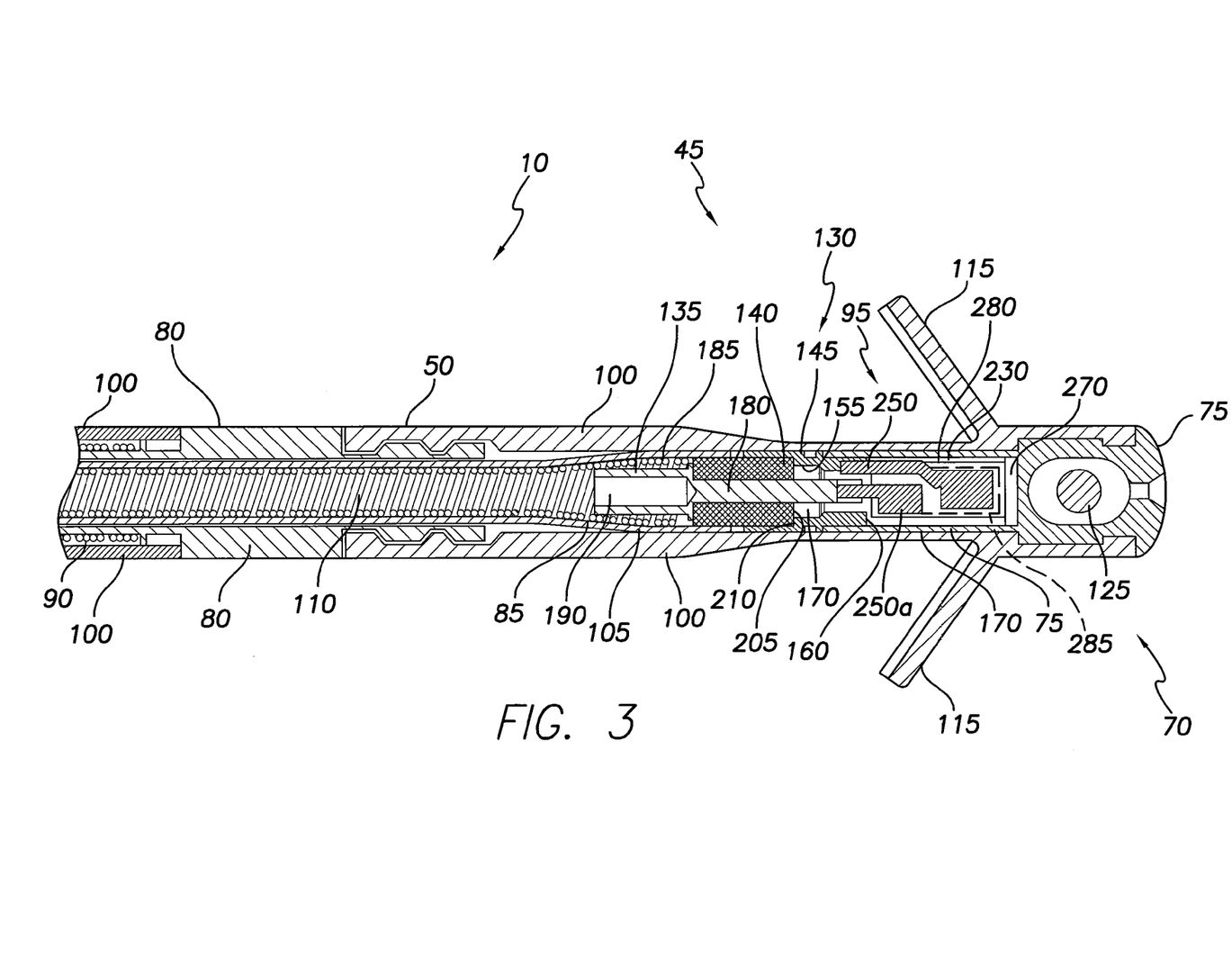
FIG. 3 is the same view as FIG. 2A, except of another embodiment.

As shown in FIG. 3, in one embodiment, the filter assembly 95 includes a plate type filter element 230 having a ceramic substrate plate 280, a printed circuit 285 on the opposite side of the ceramic plate 280 and shown in phantom lines, and terminals 250a, 250b extending off of the proximal end of the ceramic plate 280. As with the embodiment depicted in FIGS. 2A-2C, the filter element 230 may be any type of RF filter including, for example, lumped inductor filters, discrete inductor-capacitor filters, etc. Furthermore, the filter assembly 230 may include one or more filter elements 230, which may be wired in series and/or parallel.

As already mentioned, the embodiment of FIG. 3 has the same components 135, 140, 145, 75 and same general configuration relationships discussed above with respect to the embodiment of FIGS. 2A-2C. The components of the embodiment of FIG. 3 are joined in the same general arrangement and via the same methods as discussed with respect to the embodiment of FIG. 2A-2C. Thus, as can be understood from FIG. 3, in one embodiment, the feedthru 130 and tip electrode 75 are joined in such a manner so as to create a hermetically sealed chamber 270 out of the bore 270 of the proximal portion 170 of the tip electrode 75. The hermetically sealed chamber 270 may prevent the exposure of the filter assembly 95 to body fluids, avoiding electrical shorting and preventing contact between body fluids and non-bio-stable or non-bio-compatible elements.

Via methods such as welding, soldering, brazing, electrically conductive epoxy, the distal end of the pin shaft 180 is joined to one proximal terminal 250a and the other proximal terminal 250b is joined to the distal end of the flange 145. The result is an electrical circuit from the inner conductor coil 85 to the tip electrode 75 that first extends along the length of the pin 135 to the pin's distal end, which is in electrical contact with the first proximal terminal 250a. The electrical circuit then extends from the first proximal terminal 250a to the second proximal terminal 250b via the filter element 230 of the filter assembly 95. The electrical circuit then extends from the second proximal terminal 250b to the tip electrode 75 via the flange 145, which is in electrical contact with both the second proximal terminal 250b and the tip electrode 75. Thus, since the proximal end of the inner conductor coil 85 is in electrical communication with the pulse generator 15, the pulse generator and tip electrode are in electrical communication via the filter element 230. As the filter element 230 forms part of the electrical circuit extending between the pulse generator 15 and the tip electrode 75, the filter element 230 may reduce any current induced by the lead 10 being present in the magnetic field of a MRI scan. The filter assembly 95 may help to improve the heating reduction performance of the lead 10, thereby reducing the chance of tissue damage or perforation that may be caused by increased temperature of the lead tip electrode 75.

Figure 4A:
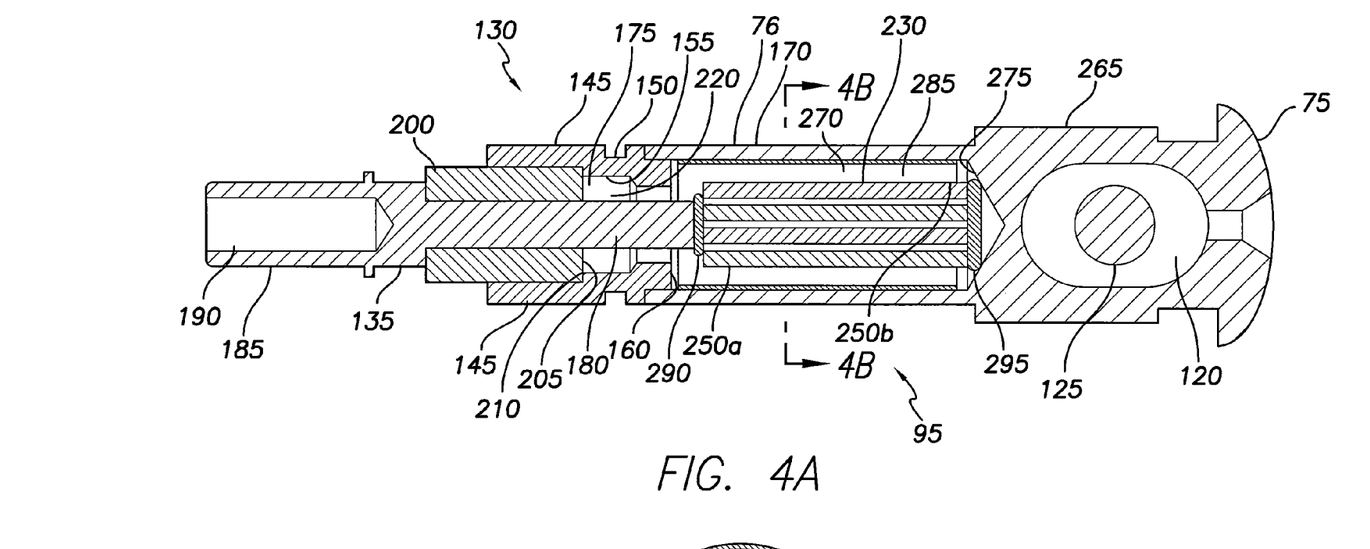
FIG. 4A is the same view as FIG. 2B, except of another embodiment.

While the embodiments depicted in FIGS. 2A-3 each have an electrical circuit extending from the inner conductor coil 85 to the tip electrode 75 that extends in order through the inner conductor coil 85, pin 135, filter assembly 95, flange 145 and tip electrode 75, in other embodiments the electrical circuit extending from the inner conductor coil 85 to the tip electrode 75 may extend directly from the pin 135 to the tip electrode 75 via the filter assembly 95. For example, as indicated in FIG. 4A, which is the same view as FIG. 2B, except of an another embodiment, the feedthru 130 has the same components 135, 140, 145 and same general configuration as the embodiment depicted in FIGS. 2A-2C, except, similar to the embodiment of FIG. 3, the pin shaft 180 does not extend through the filter assembly 95 or to the proximal-facing surface of the electrode tip bore 270. However, unlike the embodiments of FIGS. 2A-3, the embodiment of FIG. 4A has a filter assembly 95 with a configuration that allows the electrical circuit to extend directly from the pin shaft 180 to the tip electrode 75 via the filter assembly 95 and without extending through the flange 145.

Figure 4B:
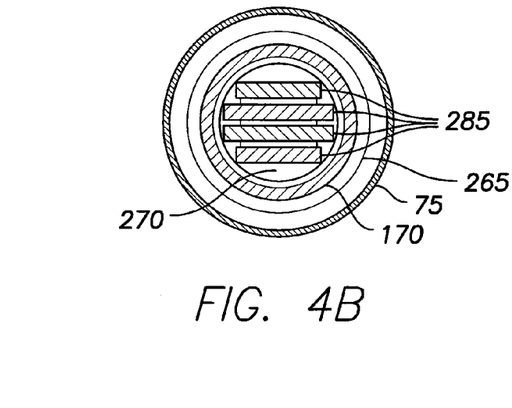
FIG. 4B is a transverse cross-section of the filter assembly as taken along section line 4B-4B in FIG. 4A.

As shown in FIG. 4A and FIG. 4B, which is a transverse cross-section of the filter assembly 95 as taken along section line 4B-4B in FIG. 4A, in one embodiment, the filter assembly 95 includes a filter element 230 that may have a number of printed circuit inductors 285 arranged in parallel and extending parallel to the axis of the tip electrode bore 270. A distal terminal 250a in the form of a bracket 250a joins together in a spaced-apart fashion the distal ends of the substrates of the printed circuit inductors 285 and causes the distal ends of the printed circuit inductors 285 to be placed in electrical communication. Similarly, a proximal terminal 250b in the form of a bracket 250b joins together in a spaced-apart fashion the proximal ends of the substrates of the printed circuit inductors 285 and causes the proximal ends of the printed circuit inductors 285 to be placed in electrical communication.

As indicated in FIG. 4A, the proximal terminal 250b is electrically coupled to the distal end of the pin shaft 180 via electrically conductive epoxy 290, soldering, welding, brazing, etc. Similarly, the distal terminal 250a is electrically coupled to the proximal-facing surface 275 via electrically conductive epoxy 290, soldering, welding, brazing, etc. It should be noted that, unlike the embodiment depicted in FIGS. 2A-2C, in the embodiment depicted in FIG. 4A, the proximal-facing surface 275 of the tip electrode bore 270 is not electrically insulated.

As with the embodiment depicted in FIGS. 2A-2C, the filter element 230 may be any type of RF filter including, for example, lumped inductor filters, discrete inductor-capacitor filters, etc. Furthermore, the filter assembly 95 may include one or more filter elements 230, which may be wired in series and/or parallel.

As already mentioned, the embodiment of FIGS. 4A and 4B has the same components 135, 140, 145, 75 and same general configuration relationships discussed above with respect to the embodiments of FIGS. 2A-3. The components of the embodiment of FIGS. 4A and 4B are joined in the same general arrangement and via the same methods as discussed with respect to the embodiments of FIG. 2A-3. Thus, as can be understood from FIGS. 4A and 4B, in one embodiment, the feedthru 130 and tip electrode 75 are joined in such a manner so as to create a hermetically sealed chamber 270 out of the bore 270 of the proximal portion 170 of the tip electrode 75. The hermetically sealed chamber 270 may prevent the exposure of the filter assembly 95 to body fluids, avoiding electrical shorting and preventing contact between body fluids and non-bio-stable or non-bio-compatible elements.

Via methods such as welding, soldering, brazing, electrically conductive epoxy, the distal end of the pin shaft 180 is joined to the proximal terminal 250a and the distal terminal 250b is joined to the electrically conductive proximal-facing surface 275 of the bore 270 of the tip electrode 75. The result is an electrical circuit from the inner conductor coil 85 to the tip electrode 75 that first extends along the length of the pin 135 to the pin's distal end, which is in electrical contact with the proximal terminal 250a. The electrical circuit then extends from the proximal terminal 250a to the distal terminal 250b via the filter element 230 of the filter assembly 95. The electrical circuit then extends directly from the distal terminal 250b to the tip electrode 75 without having to pass through the flange 145, as was the case with the embodiments discussed with respect to FIGS. 2A-3. Thus, since the proximal end of the inner conductor coil 85 is in electrical communication with the pulse generator 15, the pulse generator and tip electrode are in electrical communication via the filter element 230. As the filter element 230 forms part of the electrical circuit extending between the pulse generator 15 and the tip electrode 75, the filter element 230 may reduce any current induced by the lead 10 being present in the magnetic field of a MRI scan. The filter assembly 95 may help to improve the heating reduction performance of the lead 10, thereby reducing the chance of tissue damage or perforation that may be caused by increased temperature of the lead tip electrode 75.

The embodiments depicted in FIGS. 2A-4A each have an electrical circuit extending from the inner conductor coil 85 to the tip electrode 75, wherein FIGS. 2A-3 depict embodiments where the circuit extends, in order, through the inner conductor coil 85, pin 135, filter assembly 95, flange 145 and tip electrode 75, and the embodiment depicted in FIG. 4A has an electrical circuit extending directly from the pin 135 to the tip electrode 75 via the filter assembly 95. Still other embodiments do not use a feedthru 130 and instead, have an electrical circuit extending, in order, through the inner conductor coil 85, conductive coupler 300, filter assembly 95 and tip electrode 75. For example, as indicated in FIG. 5, which is the same view as FIG. 2B, except of an another embodiment, the embodiment of FIG. 5 has a filter assembly 95 with a configuration that allows the electrical circuit to extend directly from the inner conductor coil 85 to the tip electrode 75 via the filter assembly 95 and without employing a feedthru 130.

Figure 5:
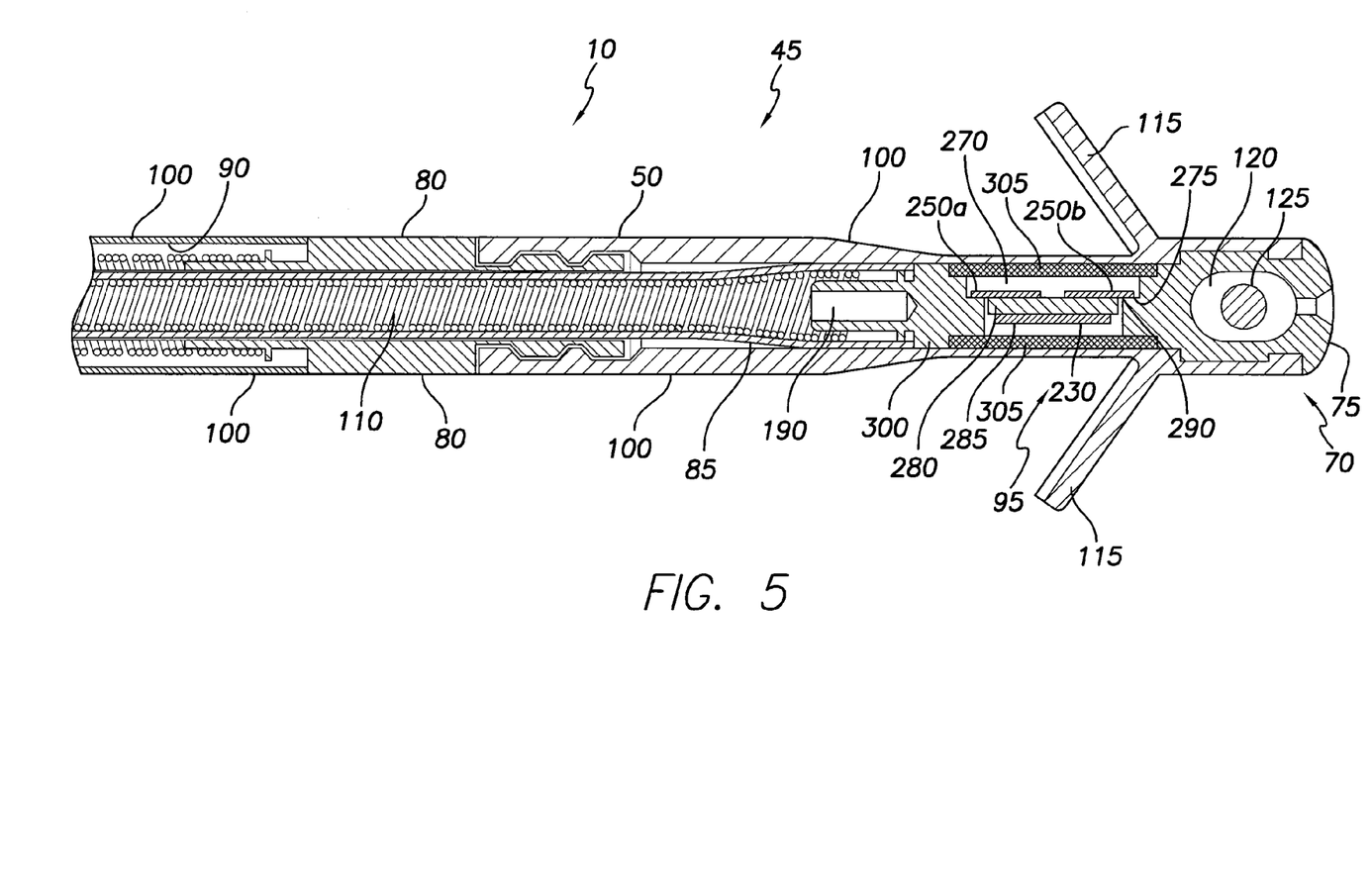
FIG. 5 is the same view as FIG. 2A, except of another embodiment and without the feedthru.

As shown in FIG. 5, in one embodiment, the filter assembly 95 includes a plate type filter element 230 having a ceramic substrate plate 280, a printed circuit 285 on a first side of the ceramic plate 280 and terminals 250a, 250b extending off of a second side of the ceramic plate 280. The printed circuit inductor 285 of the filter element 230 may extend parallel to the axis of the tip electrode bore 270. As with the embodiment depicted in FIGS. 2A-2C, the filter element 230 may be any type of RF filter including, for example, lumped inductor filters, discrete inductor-capacitor filters, etc. Furthermore, the filter assembly 95 may include one or more filter elements 230, which may be wired in series and/or parallel.

As can be understood from FIG. 5, the filter assembly 95 may be at least partially encased by a non-conductive shell 305. The non-conductive shell 305 may be cylindrical and may help to minimize the inductor shielding and parasitic capacitance effect. The non-conductive shell 305 may be made of PEEK (polyetheretherketone), polyurethane, or polysulfone.

The non-conductive shell 305 defines a hermetically sealed chamber 270. The hermetically sealed chamber 270 may prevent the exposure of the filter assembly 95 to body fluids, avoiding electrical shorting and preventing contact between body fluids and non-bio-stable or non-bio-compatible elements.

As indicated in FIG. 5, the proximal terminal 250a is electrically coupled to the distal end of the inner conductor coil 85 via a conductive coupler 300. The conductive coupler 300 may be made of platinum, titanium, or MP35 stainless steel. The distal terminal 250b is electrically coupled to the proximal-facing surface 275 of the tip electrode 75 via electrically conductive epoxy 290, soldering, welding, brazing, etc. It should be noted that, unlike the embodiment depicted in FIGS. 2A-2C, in the embodiment depicted in FIG. 5, the proximal-facing surface 275 of the tip electrode 75 is not electrically insulated.

Via a conductive coupler 300, the distal end of the inner conductor coil 85 is joined to the proximal terminal 250a and via methods such as welding, soldering, brazing, electrically conductive epoxy, the distal terminal 250b is joined to the electrically conductive proximal-facing surface 275 of the tip electrode 75. The result is an electrical circuit from the inner conductor coil 85 to the tip electrode 75 that first extends through the conductive coupler 300, which is in electrical contact with the proximal terminal 250a. The electrical circuit then extends from the proximal terminal 250a to the distal terminal 250b via the filter element 230 of the filter assembly 95. The electrical circuit then extends directly from the distal terminal 250b to the tip electrode 75. Thus, since the proximal end of the inner conductor coil 85 is in electrical communication with the pulse generator 15, the pulse generator and tip electrode are in electrical communication via the filter element 230. As the filter element 230 forms part of the electrical circuit extending between the pulse generator 15 and the tip electrode 75, the filter element 230 may reduce any current induced by the lead 10 being present in the magnetic field of a MRI scan. The filter assembly 95 may help to improve the heating reduction performance of the lead 10, thereby reducing the chance of tissue damage or perforation that may be caused by increased temperature of the lead tip electrode 75.

Figure 6:
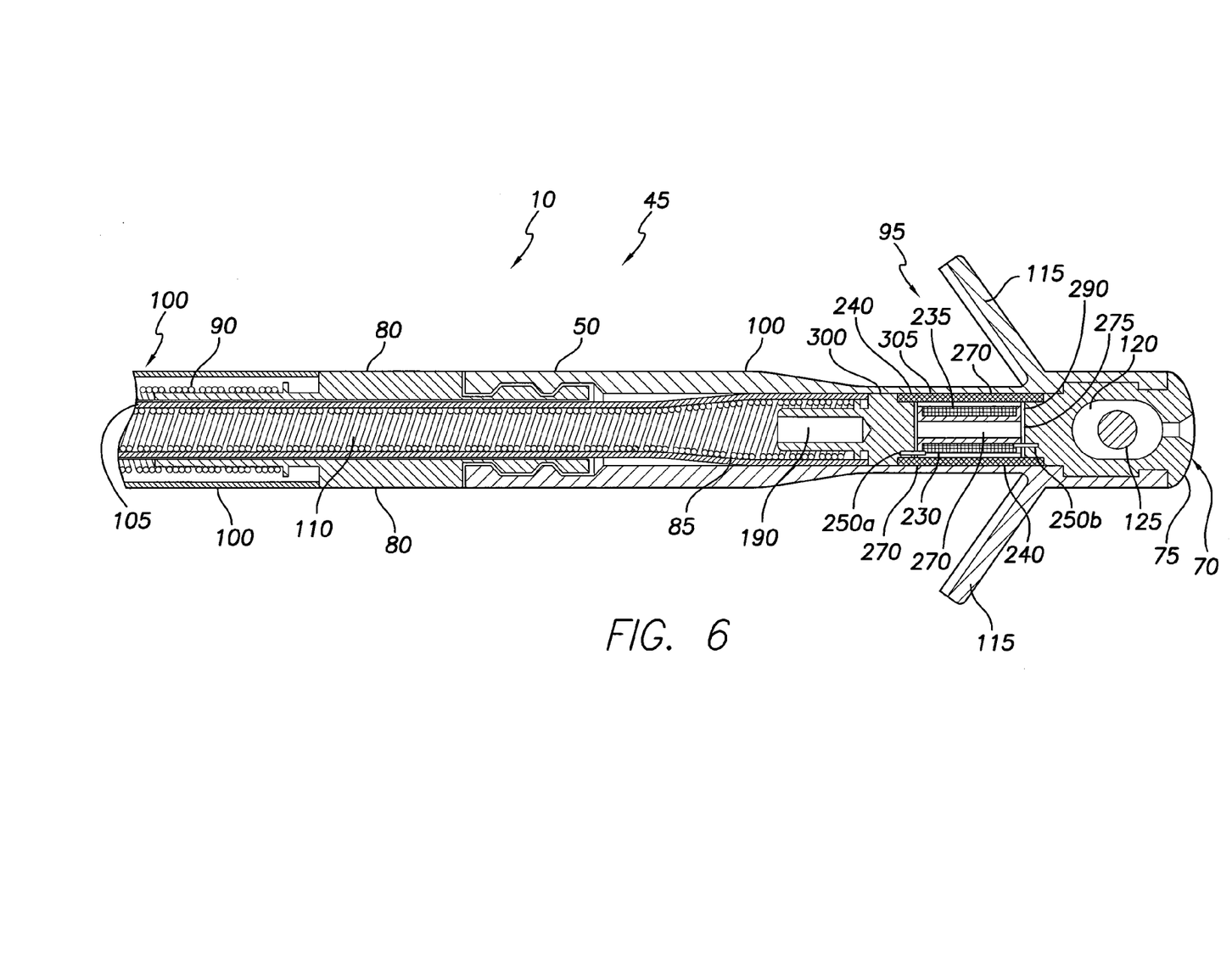
FIG. 6 is the same view as FIG. 2A, except of still another embodiment without the feedthru.

For another example of an embodiment with a filter assembly 95 with a configuration that allows the electrical circuit to extend directly from the inner conductor coil 85 to the tip electrode 75 via the filter assembly 95 and without extending through a feedthru 130, reference is now made to FIG. 6. As indicated in FIG. 6, which is the same view as FIG. 2B, except of an another embodiment, the embodiment of FIG. 6 has an electrical circuit extending, in order, through the inner conductor coil 85, conductive coupler 300, filter assembly 95 and tip electrode 75.

As shown in FIG. 6, in one embodiment, the filter assembly 95 includes a cylinder type filter element 230, a housing 235 and terminals 250a, 250b extending off of the proximal and distal sides of the filter element 230. The filter element 230 may be an induction coil or inductor/capacitor element. As with the embodiment depicted in FIGS. 2A-2C, the filter element 230 may be any type of RF filter including, for example, lumped inductor filters, discrete inductor-capacitor filters, etc. Furthermore, the filter assembly 95 may include one or more filter elements 230, which may be wired in series and/or parallel.

As shown in FIG. 6, the housing 235 may have flanged ends 240 and a cylindrical center 245 extending between the flanged ends 240, defining a location for receiving the filter element 230. As described in more detail below, the distal and proximal terminals 250a, 250b extend from the filter element 230 and through the housing 235. The housing 235 may be formed of a non-conductive material, such as ceramic, sapphire, various polymers, such as, PEEK or Delrin, or other appropriate material.

Similar to FIG. 5, the filter assembly 95 may be at least partially enclosed by a non-conductive shell 305. The non-conductive shell 305 may be cylindrical and may help to minimize the inductor shielding and parasitic capacitance effect. The non-conductive shell 305 may be made of PEEK, polyurethane, or polysulfone.

The non-conductive shell 305 defines a hermetically sealed chamber 270. The hermetically sealed chamber 270 may prevent the exposure of the filter assembly 95 to body fluids, avoiding electrical shorting and preventing contact between body fluids and non-bio-stable or non-bio-compatible elements.

As indicated in FIG. 6, the proximal terminal 250a is electrically coupled to the distal end of the inner conductor coil 85 via a conductive coupler 300. The conductive coupler 300 may be made of platinum, MP35 stainless steel, or titanium. The distal terminal 250b is electrically coupled to the proximal-facing surface 275 of the tip electrode 75 via electrically conductive epoxy 290, soldering, welding, brazing, etc. It should be noted that, unlike the embodiment depicted in FIGS. 2A-2C, in the embodiment depicted in FIG. 6, the proximal-facing surface 275 of the tip electrode 75 is not electrically insulated.

Via a conductive coupler 300, the distal end of the inner conductor coil 85 is joined to the proximal terminal 250a and via methods such as welding, soldering, brazing, electrically conductive epoxy, the distal terminal 250b is joined to the electrically conductive proximal-facing surface 275 of the tip electrode 75. The result is an electrical circuit from the inner conductor coil 85 to the tip electrode 75 that first extends through the conductive coupler 300, which is in electrical contact with the proximal terminal 250a. The electrical circuit then extends from the proximal terminal 250a to the distal terminal 250b via the filter element 230 of the filter assembly 95. The electrical circuit then extends directly from the distal terminal 250b to the tip electrode 75. Thus, since the proximal end of the inner conductor coil 85 is in electrical communication with the pulse generator 15, the pulse generator and tip electrode are in electrical communication via the filter element 230. As the filter element 230 forms part of the electrical circuit extending between the pulse generator 15 and the tip electrode 75, the filter element 230 may reduce any current induced by the lead 10 being present in the magnetic field of a MRI scan. The filter assembly 95 may help to improve the heating reduction performance of the lead 10, thereby reducing the chance of tissue damage or perforation that may be caused by increased temperature of the lead tip electrode 75.

While FIGS. 5 and 6 illustrate embodiments with a filter assembly 95 with a configuration that allows the electrical circuit to extend directly from the inner conductor coil 85 to the tip electrode 75 via the filter assembly 95, other embodiments may not extend directly to the tip electrode 75 and/or may not be inside of the tip electrode 75. For example, in FIG. 7, which is the same view as FIG. 2B, except of another embodiment, the implantable medical lead has an electrical circuit extending, in order, through the inner conductor coil 85, conductive coupler 300, filter assembly 95, distal conductor coil 310 and tip electrode 75.

Figure 7:
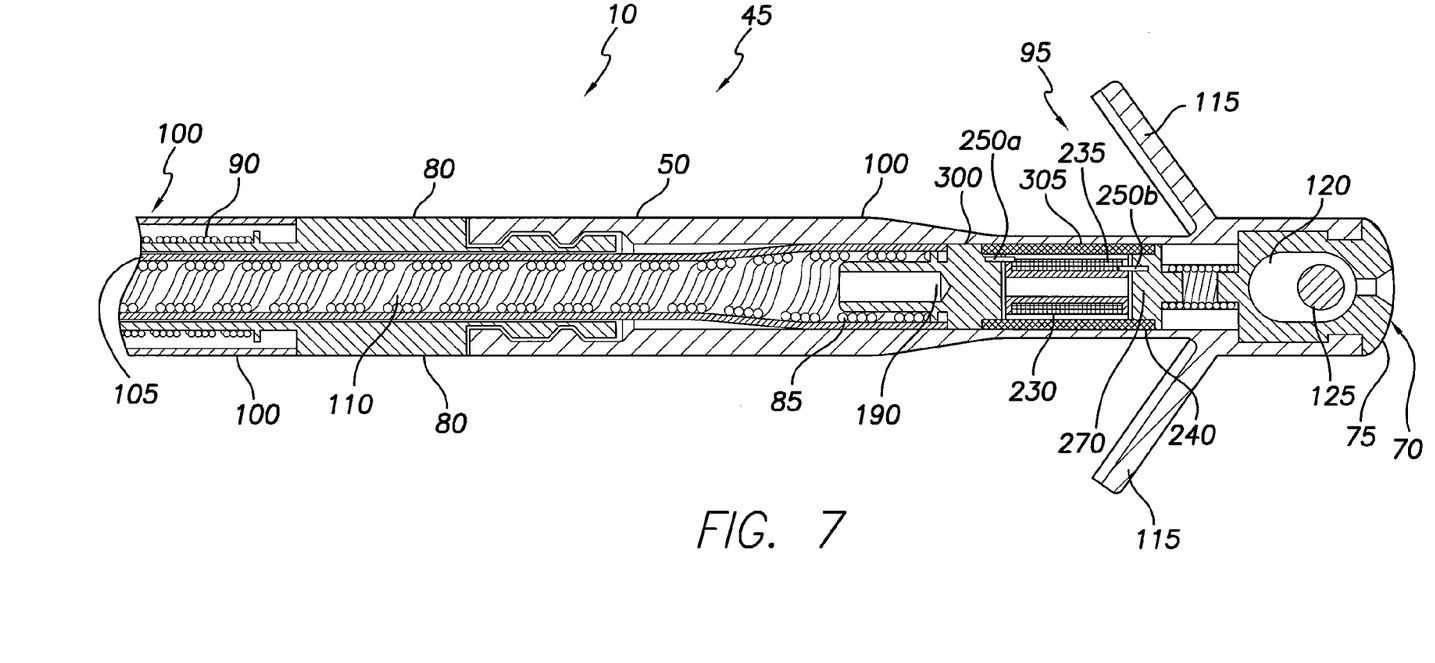
FIG. 7 is the same view as FIG. 2A, except of yet another embodiment without the feedthru.

As shown in FIG. 7, in one embodiment, the filter assembly 95 includes a cylinder type filter element 230, a housing 235 and terminals 250a, 250b extending off of proximal and distal sides of the filter element 230. The filter element 230 may be an induction coil or inductor/capacitor element. As with the embodiment depicted in FIGS. 2A-2C, the filter element 230 may be any type of RF filter including, for example, lumped inductor filters, discrete inductor-capacitor filters, etc. Furthermore, the filter assembly 95 may include one or more filter elements 230, which may be wired in series and/or parallel.

As illustrated in FIG. 7, the housing 235 may have flanged ends 240 and a cylindrical center 245 extending between the flanged ends 240, defining a location for receiving the filter element 230. As described in more detail below, the distal and proximal terminals 250a, 250b extend from the filter element 230 and through the housing 235. The housing 235 may be formed of a non-conductive material, such as ceramic, sapphire, various polymers, such as, PEEK or Delrin, or other appropriate material.

Similar to FIGS. 5 and 6, the filter assembly 95 may be at least partially enclosed by a non-conductive shell 305. The non-conductive shell 305 may be cylindrical and may help to minimize the inductor shielding and parasitic capacitance effect. The non-conductive shell 305 may be made of PEEK, polyurethane, or polysulfone.

The non-conductive shell 305 defines a hermetically sealed chamber 270. The hermetically sealed chamber 270 may prevent the exposure of the filter assembly 95 to body fluids, avoiding electrical shorting and preventing contact between body fluids and non-bio-stable or non-bio-compatible elements.

As indicated in FIG. 7, the proximal terminal 250a is electrically coupled to the distal end of the inner conductor coil 85 via a conductive coupler 300. The conductive coupler 300 may be platinum, MP35 stainless steel, or titanium. The distal terminal 250b is electrically coupled to the tip electrode 75 via a conductor coil or cable 310. That is, the filter assembly 95 is separated from the tip electrode 75 by the conductor coil or cable 310.

Via a conductive coupler 300, the distal end of the inner conductor coil 85 is joined to the proximal terminal 250a and via a conductor coil or cable 310, the distal terminal 250b is joined to the tip electrode 75. The result is an electrical circuit from the inner conductor coil 85 to the tip electrode 75 that first extends through the conductive coupler 300, which is in electrical contact with the proximal terminal 250a. The electrical circuit then extends from the proximal terminal 250a to the distal terminal 250b via the filter element 230 of the filter assembly 95. The electrical circuit then extends from the distal terminal 250b to the tip electrode 75 via the conductor cable or coil 310. Thus, since the proximal end of the inner conductor coil 85 is in electrical communication with the pulse generator 15, the pulse generator and tip electrode are in electrical communication via the filter element 230. As the filter element 230 forms part of the electrical circuit extending between the pulse generator 15 and the tip electrode 75, the filter element 230 may reduce any current induced by the lead 10 being present in the magnetic field of a MRI scan. The filter assembly 95 may help to improve the heating reduction performance of the lead 10, thereby reducing the chance of tissue damage or perforation that may be caused by increased temperature of the lead tip electrode 75.

The embodiments discussed with respect to FIGS. 2A-7 illustrate lead distal tips having a passive fixation configuration. However, it should be noted that the features depicted in, and discussed with respect to, FIGS. 2A-7 may be readily employed with lead distal tips having an active fixation configuration similar to the anchor 605 depicted in FIGS. 8A-8B. Therefore the embodiments disclosed in FIGS. 2A-7 should not be limited to one type of fixation configuration or another, but should be considered to encompass both passive and active fixation leads.

Figure 8A:
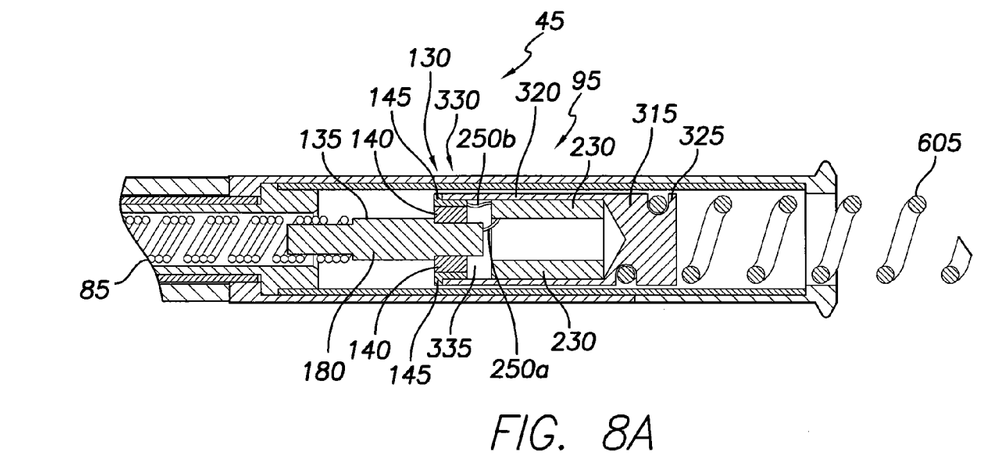
FIG. 8A is an enlarged cross-sectional view of an embodiment of the filter assembly of FIG. 2A, wherein the lead includes an anchor.
Figure 8B:
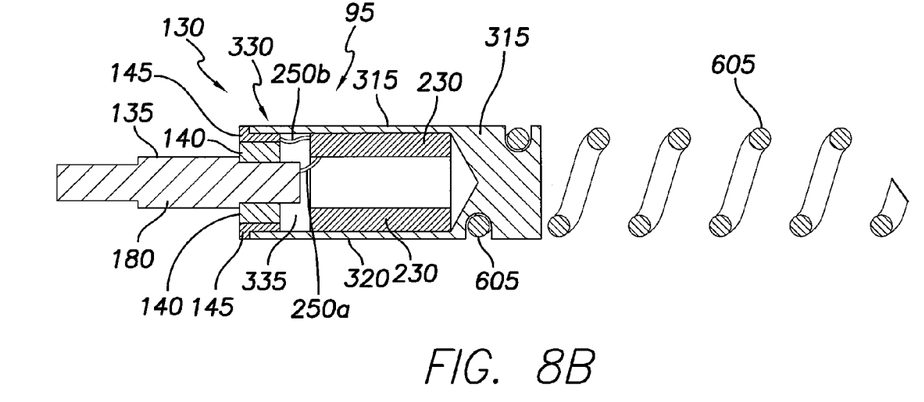
FIG. 8B is an enlarged view of the feedthru, filter assembly and the anchor of FIG. 8A.

For an example of a lead distal tip having an active fixation configuration and a filter assembly, reference is now made to FIG. 8A, which is an enlarged cross-sectional view of an embodiment of the filter assembly similar to that of FIG. 2A and including an anchor. Reference is also made to FIG. 8B, which is an enlarged view of the feedthru, filter assembly and the anchor of FIG. 8A.

As shown in FIGS. 8A-8B, in one embodiment, the filter assembly 95 includes a cylinder type filter element 230 and terminals 250a, 250b extending off of a proximal side of the filter element 230. The filter element 230 may be an induction coil or inductor/capacitor element. As with the embodiment depicted in FIGS. 2A-2C, the filter element 230 may be any type of RF filter including, for example, lumped inductor filters, discrete inductor-capacitor filters, etc. Furthermore, the filter assembly 95 may include one or more filter elements 230, which may be wired in series and/or parallel.

The embodiment of FIG. 8A has the same components 135, 140, 145 and same general configuration relationships discussed above with respect to the embodiment of FIGS. 2A-2C, except replacing the tip electrode 75 of FIGS. 2A-2C with an anchor tip electrode 605. For example, instead of a tip electrode 75, the embodiment of FIGS. 8A-8B includes a casing 315 and an anchor 605. A proximal end 320 of the casing 315 may be received by the flange 145. A distal end 325 of the casing 315 may be configured to receive an anchor 605. The proximal portion 330 of the casing 315 defines a bore 335. The casing may be made of platinum, MP35 stainless steel, or titanium.

The components of the embodiment of FIG. 8A are joined in the same general arrangement and via the same methods as discussed with respect to the embodiment of FIG. 2A-2C. Thus, as can be understood from FIGS. 8A-8B, in one embodiment, the feedthru 130 and casing 315 are joined in such a manner so as to create a hermetically sealed chamber 335 out of the bore 335 of the proximal portion 330 of the casing 315. The hermetically sealed chamber 335 may prevent the exposure of the filter assembly 95 to body fluids, avoiding electrical shorting and preventing contact between body fluids and non-bio-stable or non-bio-compatible elements.

Via methods such as welding, soldering, brazing, electrically conductive epoxy, the distal end of the pin shaft 180 is joined to one proximal terminal 250a and the proximal terminal 250b is joined to the distal end of the flange 145. The result is an electrical circuit from the inner conductor coil 85 to the anchor 605 that first extends along the length of the pin 135 to the pin's distal end, which is in electrical contact with the first proximal terminal 250a. The electrical circuit then extends from the first proximal terminal 250a to the second proximal terminal 250b via the filter element 230 of the filter assembly 95. The electrical circuit then extends from the second proximal terminal 250b to the anchor 605 via the flange 145 and the casing 315. The flange 145 is in electrical contact with both the second proximal terminal 250b and the casing 315, and the casing 315 is in electrical contact with the anchor 605. Thus, since the proximal end of the inner conductor coil 85 is in electrical communication with the pulse generator 15, the pulse generator and anchor are in electrical communication via the filter element 230. As the filter element 230 forms part of the electrical circuit extending between the pulse generator 15 and the anchor 605, the filter element 230 may reduce any current induced by the lead 10 being present in the magnetic field of a MRI scan. The filter assembly 95 may help to improve the heating reduction performance of the lead 10, thereby reducing the chance of tissue damage or perforation that may be caused by increased temperature of the anchor 605.

Although the present invention has been described with reference to preferred embodiments, persons skilled in the art will recognize that changes may be made in form and detail without departing from the spirit and scope of the invention.

What is claimed is:

1. An implantable medical lead comprising:
    a tubular body including a proximal end and a distal end;
    a lead connector near the proximal end;
    a conductor extending longitudinally within the tubular body, the conductor having a proximal end that is electrically coupled to the connector;
    a contact pin electrically coupled to a distal end of the conductor;
    a filter element electrically coupled to a distal end of the contact pin;
    a flange electrically coupled to a proximal end of the filter element; and
    an electrode, wherein a proximal portion of the electrode is electrically coupled to the flange so as to form at least a first part of a hermetic chamber enclosing the filter element.

2. The lead of claim 1, wherein the filter element includes a plurality of coils.

3. The lead of claim 2, wherein the contact pin extends through the plurality of coils.

4. The lead of claim 1, wherein at least a portion of the filter element resides within the proximal portion of the electrode.

5. The lead of claim 1 further comprising an insulator coupled between the flange and the contact pin, wherein the contact pin extends through the flange and is in electrical isolation from the flange.

6. The lead of claim 5 wherein the insulator and the contact pin form at least a second part of the hermetic chamber enclosing the filter element and wherein the flange and the insulator form at least a third part of the hermetic chamber enclosing the filter element.

7. The lead of claim 1, wherein the electrode includes at least one of a non-anchor tip electrode and an anchor tip electrode.

8. The lead of claim 1, wherein the filter element includes at least one of a lumped inductor, a discrete inductor capacitor, an inductor coil, and a printed circuit.

9. The implantable lead of claim 1 wherein a second proximal end of the filter element is electrically coupled to the distal end of the contact pin.

10. The implantable lead of claim 1 wherein a distal end of the filter element is electrically coupled to the distal end of the contact pin.

11. The implantable lead of claim 1 wherein a proximal end of the filter element is electrically coupled to the distal end of the contact pin and a distal end of the filter element is electrically coupled to the electrode.

12. An implantable medical lead comprising:
 a tubular body including a proximal end and a distal end;
 a lead connector near the proximal end;
 a conductor extending longitudinally within the tubular body, the conductor having a proximal end that is electrically coupled to the connector;
 a conductive coupler electrically coupled to a distal end of the conductor;
 a filter element having a proximal end electrically coupled to a distal end of the conductive coupler;
 an electrode electrically coupled to a distal end of the filter element; and
 a non-electrically conductive shell enclosing at least a portion of the filter element and longitudinally spacing the conductive coupler from the electrode, wherein the non-electrically conductive shell forms at least part of a hermetic chamber enclosing the filter element.

13. The lead of claim 12, wherein the electrode includes at least one of a non-anchor tip electrode and an anchor tip electrode.

14. The lead of claim 12, wherein the filter element includes at least one of a lumped inductor, a discrete inductor capacitor, an inductor coil, and a printed circuit.

15. The lead of claim 12, wherein the electrical circuit further includes a second at least one of a coiled conductor, a wire and a cable located along the electrical circuit between the distal end of the filter element and the electrode.

* * * * *